(12) United States Patent
Tatebayashi et al.

(10) Patent No.: US 12,022,997 B2
(45) Date of Patent: Jul. 2, 2024

(54) DISTAL END HOOD, ENDOSCOPE, AND OBSERVATION METHOD USING ENDOSCOPE

(71) Applicant: OLYMPUS CORPORATION, Tokyo (JP)

(72) Inventors: Takaaki Tatebayashi, Tokyo (JP); Seisuke Takase, Hachioji (JP); Naohiro Nakamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 648 days.

(21) Appl. No.: 17/083,431

(22) Filed: Oct. 29, 2020

(65) Prior Publication Data

US 2021/0100433 A1 Apr. 8, 2021

Related U.S. Application Data

(63) Continuation of application No. PCT/JP2019/007100, filed on Feb. 25, 2019.

(30) Foreign Application Priority Data

Jun. 1, 2018 (JP) .................................. 2018-106167

(51) Int. Cl.
*A61B 1/00* (2006.01)
(52) U.S. Cl.
CPC ...... *A61B 1/00089* (2013.01); *A61B 1/00096* (2013.01)
(58) Field of Classification Search
CPC .............. A61B 1/0008; A61B 1/00089; A61B 1/00101; A61B 1/00096; A61B 1/00135;
(Continued)

(56) References Cited

U.S. PATENT DOCUMENTS 5,897,487 A * 4/1999 Ouchi ................ A61B 1/00137
600/129
6,916,284 B2 * 7/2005 Moriyama ........... A61B 5/6886
600/129
(Continued)

FOREIGN PATENT DOCUMENTS

EP          2057930 A1     5/2009
JP       2005-52359 A     3/2005
(Continued)

OTHER PUBLICATIONS

International Search Report dated May 7, 2019 issued in PCT/JP2019/007100.

*Primary Examiner* — Ryan N Henderson
(74) *Attorney, Agent, or Firm* — Scully, Scott, Murphy & Presser, P.C.

(57) ABSTRACT

A distal end hood that is detachably mounted on a distal end portion of an endoscope includes a groove having a groove bottom portion formed in a ring shape over an entire circumference at a predetermined position on an outer peripheral surface of the distal end hood, a plurality of projections, which are provided on an inner peripheral surface on one side sandwiching the groove and in each of which a tapered surface is formed, the tapered surface reducing a wall thickness by continuously increasing a diameter of an inner peripheral surface from the groove side toward a distal end surface of the distal end hood, and a locking portion provided on a side opposite to the projections sandwiching the groove and locked to the distal end portion of the endoscope, in which the projections are configured to bend at the groove bottom portion toward a proximal end side.

20 Claims, 7 Drawing Sheets

(58) Field of Classification Search
CPC ........... A61B 1/00142; A61B 1/00154; A61M 3/0291; A61M 29/00; A61M 29/02
See application file for complete search history.

(56) References Cited

U.S. PATENT DOCUMENTS

| | | | | |
|---|---|---|---|---|
| 7,507,200 B2* | 3/2009 | Okada | ............... | A61B 1/012 600/129 |
| 7,988,619 B2* | 8/2011 | Longo | ............... | A61B 1/32 606/198 |
| 8,337,394 B2* | 12/2012 | Vakharia | ............... | A61B 1/00135 600/114 |
| 2002/0035311 A1* | 3/2002 | Ouchi | ............... | A61B 1/00089 600/156 |
| 2003/0088154 A1* | 5/2003 | Ishibiki | ............... | A61B 1/042 600/127 |
| 2004/0073089 A1* | 4/2004 | Nozue | ............... | A61B 1/00089 600/127 |
| 2004/0082832 A1* | 4/2004 | Moriyama | ............... | A61B 1/00089 600/101 |
| 2004/0267092 A1* | 12/2004 | Ishibiki | ............... | A61B 1/00089 600/127 |
| 2005/0043584 A1* | 2/2005 | Nozue | ............... | A61B 1/00089 600/127 |
| 2009/0156898 A1* | 6/2009 | Ichimura | ............... | A61B 1/00096 600/127 |
| 2010/0081877 A1* | 4/2010 | Vakharia | ............... | A61B 1/3132 600/129 |
| 2015/0148606 A1* | 5/2015 | Rottenberg | ............... | A61B 17/0218 600/114 |
| 2016/0038133 A1* | 2/2016 | Smith | ............... | A61B 17/320016 600/204 |
| 2017/0112365 A1* | 4/2017 | Ostrovsky | ............... | A61B 1/31 |
| 2017/0119234 A1* | 5/2017 | Petroskey | ............... | A61B 17/0218 |
| 2018/0168437 A1* | 6/2018 | Schreiner | ............... | A61B 1/00128 |
| 2019/0183328 A1* | 6/2019 | Axon | ............... | A61B 1/31 |
| 2020/0022563 A1* | 1/2020 | Sugita | ............... | A61B 1/00165 |
| 2020/0060517 A1* | 2/2020 | Roychowdhury | . | A61B 1/00103 |
| 2020/0060518 A1* | 2/2020 | Roychowdhury | . | A61B 1/00147 |
| 2021/0085171 A1* | 3/2021 | Zhang | ............... | A61B 1/0011 |

FOREIGN PATENT DOCUMENTS

| | | |
|---|---|---|
| JP | 2008-54843 A | 3/2008 |
| JP | 5030507 B2 | 9/2012 |
| JP | 2013-99466 A | 5/2013 |

* cited by examiner

DISTAL END HOOD, ENDOSCOPE, AND OBSERVATION METHOD USING ENDOSCOPE

CROSS REFERENCE TO RELATED APPLICATION

This application is a continuation application of PCT/JP2019/007100 filed on Feb. 25, 2019 and claims benefit of Japanese Application No. 2018-106167 filed in Japan on Jun. 1, 2018, the entire contents of which are incorporated herein by this reference.

BACKGROUND OF THE INVENTION

1. Field of the Invention

The present invention relates to a distal end hood mounted on a distal end portion of an insertion portion of an endoscope, an endoscope, and an observation method using the endoscope.

2. Description of the Related Art

Endoscopes have been used in the medical field, industrial field, and the like.

In recent years, for example, in early detection, diagnosis, and treatment of lesions such as cancer, an endoscope capable of magnifying observation (for example, approximately 100 times) or super-magnifying observation (magnification at the histological observation level, for example, approximately 500 times) of lesions or the like under the endoscope has been attracting attention.

At the time of the super-magnifying observation, a user performs an observation by bringing a lens surface of an observation optical system into contact with a subject to hold an endoscope distal end portion in a stable state. On the other hand, at the time of the magnifying observation, the user performs an observation by holding a distance between the lens surface and a surface of a living tissue at an observation depth (several millimeters).

Japanese Patent No. 5030507 discloses a distal end hood of an endoscope in which an elastically deformable portion that is elastically deformable is disposed at a distal end portion of a tubular hood body whose proximal end portion is mounted on an outer peripheral surface of a distal end portion of the endoscope.

The distal end hood has the hood body, and the hood body is provided with a mounting portion at the proximal end portion and the elastically deformable portion that is elastically deformable at the distal end portion. The hood body is made of a relatively hard resin material, and the elastically deformable portion is made of a resin material or a rubber material that is softer than the hood body.

According to the distal end hood, the lens can be positioned at the observation position by bringing the distal end portion of the elastically deformable portion into contact with the subject, and the lens can be brought into contact with the subject by elastically deforming the elastically deformable portion.

SUMMARY OF THE INVENTION

A distal end hood of one aspect of the present invention is a distal end hood that is detachably mounted on a distal end portion of an endoscope, and includes a groove having a groove bottom portion formed in a ring shape over an entire circumference at a predetermined position on an outer peripheral surface of the distal end hood, a plurality of projections, which are provided on an inner peripheral surface on one side sandwiching the groove and in each of which an inclined surface is formed, the inclined surface reducing a wall thickness by increasing a diameter of the inner peripheral surface from the groove side toward an end surface on the one side, and a locking portion provided on a side opposite to the projections sandwiching the groove and locked to the distal end portion of the endoscope, in which the projections are configured to bend at the groove bottom portion toward a proximal end side.

An endoscope of one aspect of the present invention includes a distal end hood that is mounted on a distal end portion of the endoscope. The distal end hood includes a groove having a groove bottom portion formed in a ring shape over an entire circumference at a predetermined position on an outer peripheral surface of the distal end hood, a plurality of projections, which are provided on an inner peripheral surface on one side sandwiching the groove and in each of which an inclined surface is formed, the inclined surface reducing a wall thickness by increasing a diameter of the inner peripheral surface from the groove side toward an end surface on the one side, the plurality of projections being configured to bend at the groove bottom portion toward a proximal end side, and a locking portion provided on a side opposite to the projections sandwiching the groove and locked to the distal end portion of the endoscope.

In an observation method using an endoscope of an aspect of the present invention, a plurality of projections provided in a distal end hood are bent at a distal end surface of a distal end lens of the endoscope toward a proximal end side, and a subject is observed in a state in which the distal end lens is in contact with the subject.

DETAILED DESCRIPTION OF THE PREFERRED EMBODIMENTS

Figure 1:
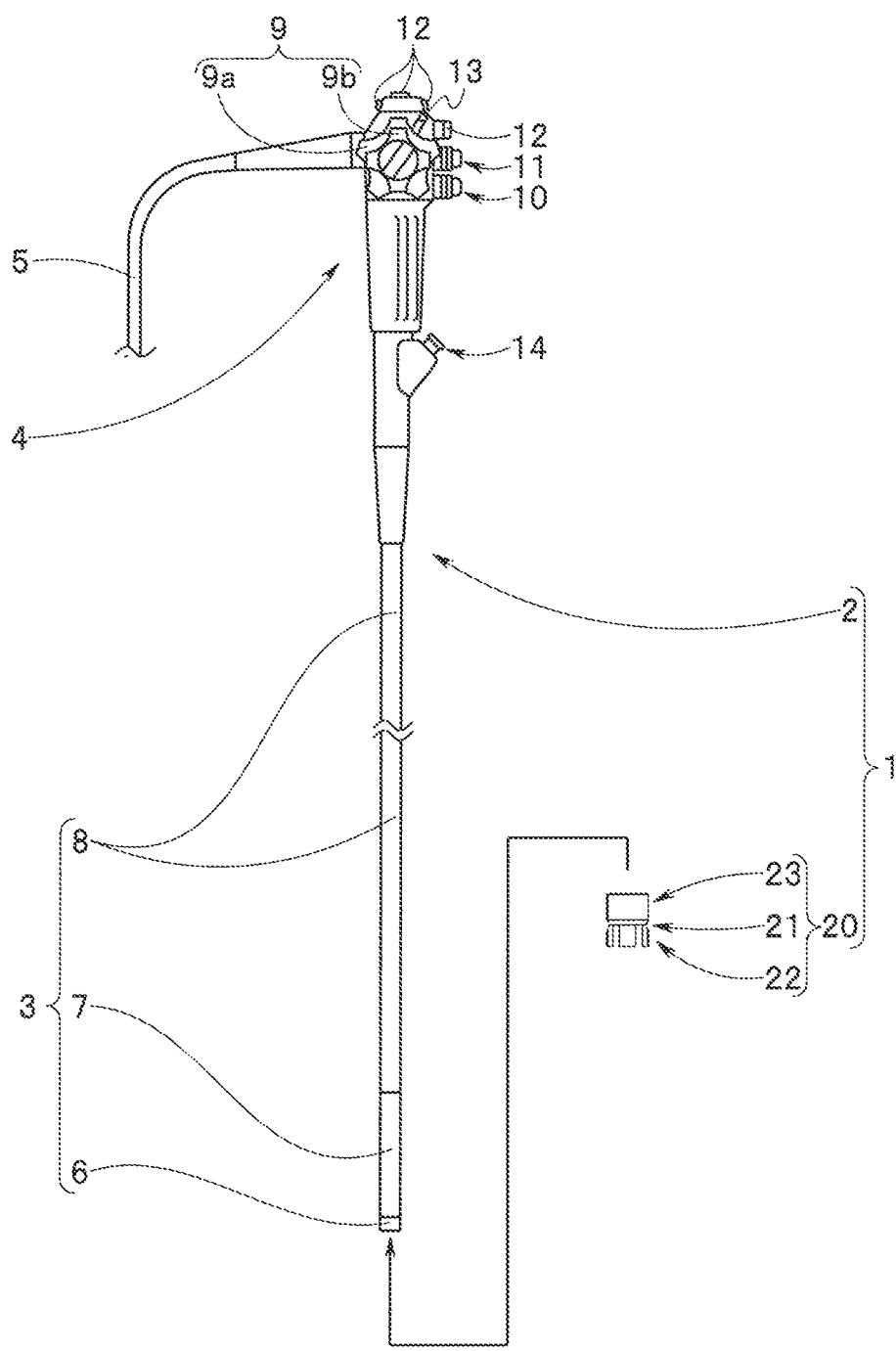
FIG. 1 is a diagram illustrating an endoscope system including an endoscope and a distal end hood.

Hereinafter, embodiments of the present invention will be described with reference to the accompanying drawings.

Note that, in each of the drawings used in the following description, in order to make each component recognizable on the drawing, the scale may be different for each component. In other words, the present invention is not limited to the number of components, the shape of the components, the ratio of the sizes of the components, and the relative positional relationship of the components described in the drawings.

An endoscope system 1 illustrated in FIG. 1 includes an endoscope 2 and a distal end hood 20. The endoscope 2 includes an objective lens (reference numeral 62 in FIG. 3) that enables observation by being brought into contact with an observation target.

The endoscope 2 mainly includes an insertion portion 3 and an operation portion 4 provided on a proximal end side of the insertion portion 3. A universal cord 5 extends from a side portion of the operation portion 4.

The insertion portion 3 of the endoscope 2 includes a distal end portion 6, a bending portion 7, and a flexible tube portion 8 having flexibility that are connected in series from a distal end side. The distal end portion 6 is hard. Inside the distal end portion 6, an observation optical system (refer to reference numeral 60 in FIG. 3 and the like) provided with a movable lens frame (refer to reference numeral 61 in FIG. 3), and an illumination optical system are provided. The bending portion 7 is configured to bend the distal end portion 6, for example, in the vertical and horizontal directions.

The operation portion 4 of the endoscope 2 is provided with a bending operation device 9 having a vertical bending operation knob 9a and a horizontal bending operation knob 9b, an air/water feeding control unit 10, a suction control unit 11, a plurality of switches 12, an operating lever 13, and a forceps opening 14.

The plurality of switches 12 include a freeze switch for generating a freeze signal, a release switch for generating a release signal when shooting a picture, an observation mode changeover switch for giving an observation mode change instruction, and the like.

The operating lever 13 is a magnification changing lever that moves backward and forward the movable lens frame 61 provided in the observation optical system.

One end portion of a treatment instrument channel which is a conduit (see reference numeral 15 in FIG. 3) configured to reach the distal end of the insertion portion from the hand side of the endoscope, is connected with the forceps opening 14. The other end portion of the treatment instrument channel is connected with a treatment instrument channel mouthpiece (see reference numeral 17 in FIG. 3) that connects with a treatment instrument opening (see reference numeral 16 in FIG. 3 and the like) provided on a distal end surface 6a of the distal end portion 6.

The distal end hood 20 is detachably mounted on the distal end portion 6 of the endoscope 2. The distal end hood 20 is made of resin or rubber having a predetermined elastic force, and is formed of, for example, silicone rubber with predetermined rubber hardness.

Figure 2A:
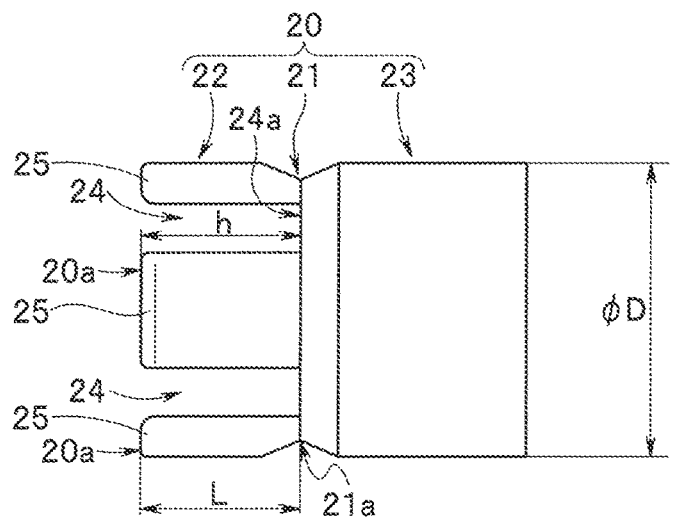
FIG. 2A is an enlarged view illustrating the distal end hood of FIG. 1.

As illustrated in FIGS. 1 and 2A, the distal end hood 20 is provided with a peripheral groove 21 formed in a ring shape over the entire circumference at a predetermined position on an outer peripheral surface. The peripheral groove 21 divides the outer peripheral surface of the distal end hood 20 into a front outer peripheral surface and a rear outer peripheral surface. A groove bottom portion 21a of the peripheral groove 21 is provided at a position separated from a hood distal end surface 20a by a distance L. The peripheral groove 21 is a V-groove having a V-shaped cross-section. The cross-sectional shape of the peripheral groove 21 is not limited to the V-shape, but the groove may have, for example, a bottom having an R shape or formed in a circumferential surface.

The distal end hood 20 is provided with a protruding portion 22 having the front outer peripheral surface, and a locking portion 23 having the rear outer peripheral surface, with the peripheral groove 21 interposed therebetween. In other words, the distal end hood 20 is provided with the protruding portion 22 on one side, and the locking portion 23 on the opposite side of the protruding portion 22, with the peripheral groove 21 interposed therebetween. The locking portion 23 has a tubular shape and is fixed to the distal end portion 6 of the endoscope 2 by elastic force.

Figure 2B:
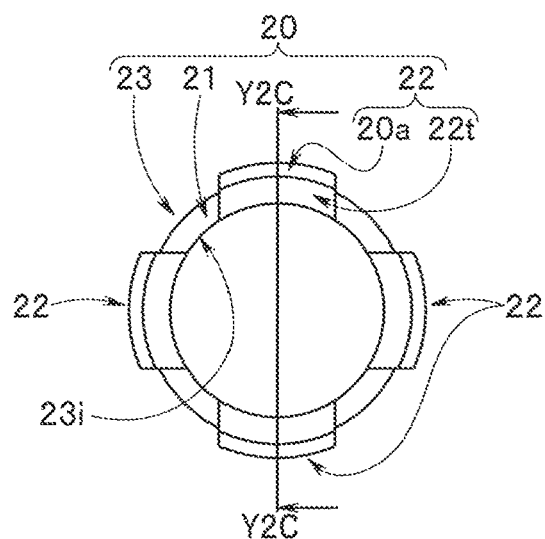
FIG. 2B is a front view of the distal end hood of FIG. 2A as viewed from the direction of arrow Y2B.

The protruding portion 22 is divided into four rectangular-shaped projection portions 25 by a plurality of cutouts 24 extending from a side of the hood distal end surface 20a, which is an end surface on one side, to a front side of the locking portion 23. As illustrated in FIG. 2B, the four projection portions 25 are arranged at equal intervals in the circumferential direction.

Figure 5:
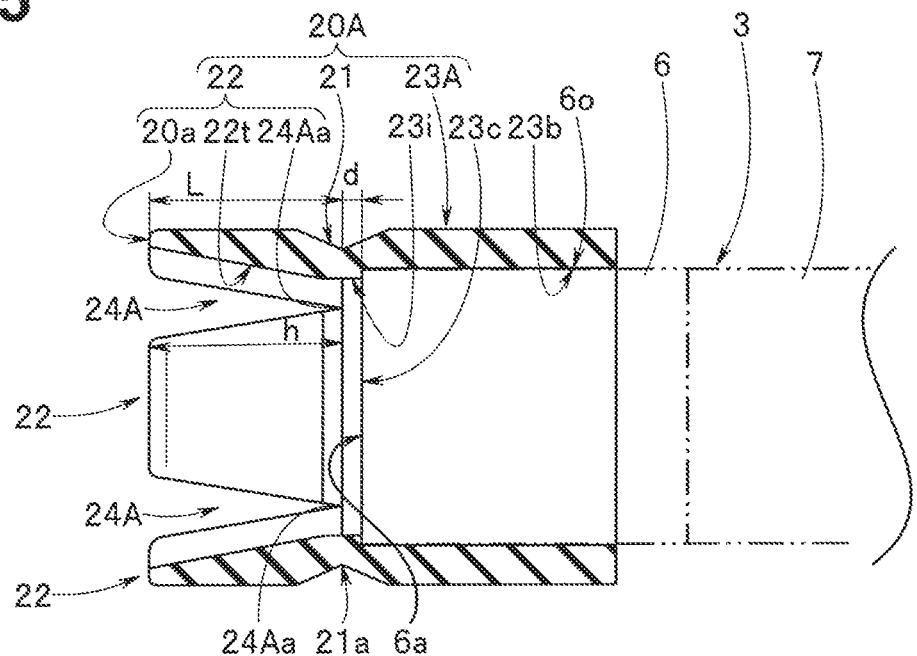
FIG. 5 is a diagram illustrating a locking recessed portion provided on an inner circumference of a locking portion.

Note that the number of the projection portions 25 formed by providing the cutouts 24 is not limited to four, but may be two, three, four, or more. In addition, the shape of the projection portion 25 is not limited to the rectangular shape, but may be a mountain shape (also referred to as a trapezoidal shape) or the like by a cutout 24A as illustrated in FIG. 5. The ridgeline of the projection portion 25 is rounded to prevent damage to body tissues and the like.

The peripheral groove 21 formed on the front outer peripheral surface of each projection portion 25 functions as a valley fold portion 25V that is a hinge when the projection portion 25 is bent outward with respect to the locking portion 23.

As illustrated in FIG. 2A, the depth from the hood distal end surface 20a to the cutout bottom portion 24a of the cutout 24 is h. Then, h and L are set to be the same.

Figure 2C:
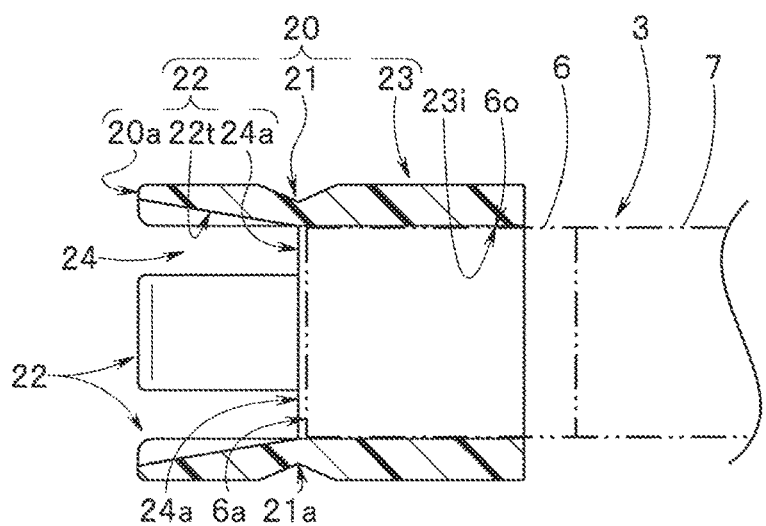
FIG. 2C is a cross-sectional view taken along arrow Y2C-Y2C of FIG. 2B.

When performing super-magnifying observation or magnifying observation with the endoscope 2, as illustrated in FIG. 2C, an inner peripheral surface 23i of the locking portion 23 is locked to an outer peripheral surface 6o of the distal end portion 6 of the insertion portion 3 indicated by the two-dot chain line.

In the hood-mounted state in which the locking portion 23 is locked to the distal end portion 6, the groove bottom portion 21a of the peripheral groove 21 is disposed on a front side of the distal end surface 6a of the distal end portion 6.

The arrangement state is implemented by disposing the cutout bottom portion 24a on the front side of the distal end surface 6a of the distal end portion 6 when the hood is mounted.

A wall thickness of the locking portion 23 is uniform. On the other hand, the wall thickness of the protruding portion 22 becomes continuously thinner toward the front. Specifically, an inner peripheral surface of the protruding portion 22 is a tapered surface 22t, and the inner diameter of the protruding portion 22 continuously increases from the inner peripheral surface in the vicinity of the groove bottom portion 21a toward the inner peripheral surface at the hood distal end surface 20a. Note that, instead of the tapered surface 22t, an inner peripheral edge of the hood distal end surface 20a may be chamfered.

Note that a locking portion outer diameter of the locking portion 23 and a protruding portion outer diameter of the protruding portion 22 are set to be the same or substantially the same. In the figure, the locking portion outer diameter and the protruding portion outer diameter are set to D.

Here, the operation of the distal end hood 20 will be described.

When performing the super-magnifying observation or the magnifying observation, an operator locks the inner peripheral surface 23i of the locking portion 23 of the distal end hood 20 to the outer peripheral surface 6o of the distal end portion 6. At this time, as described above, the position of the cutout bottom portion 24a is disposed on the front side of the distal end surface 6a of the distal end portion 6, so that the groove bottom portion 21a is disposed on the front side of the distal end surface 6a of the distal end portion 6. At this time, the groove bottom portion 21a is substantially aligned with a lens distal end surface 62a of the distal end lens 62 protruding from the distal end surface 6a.

Figure 3:
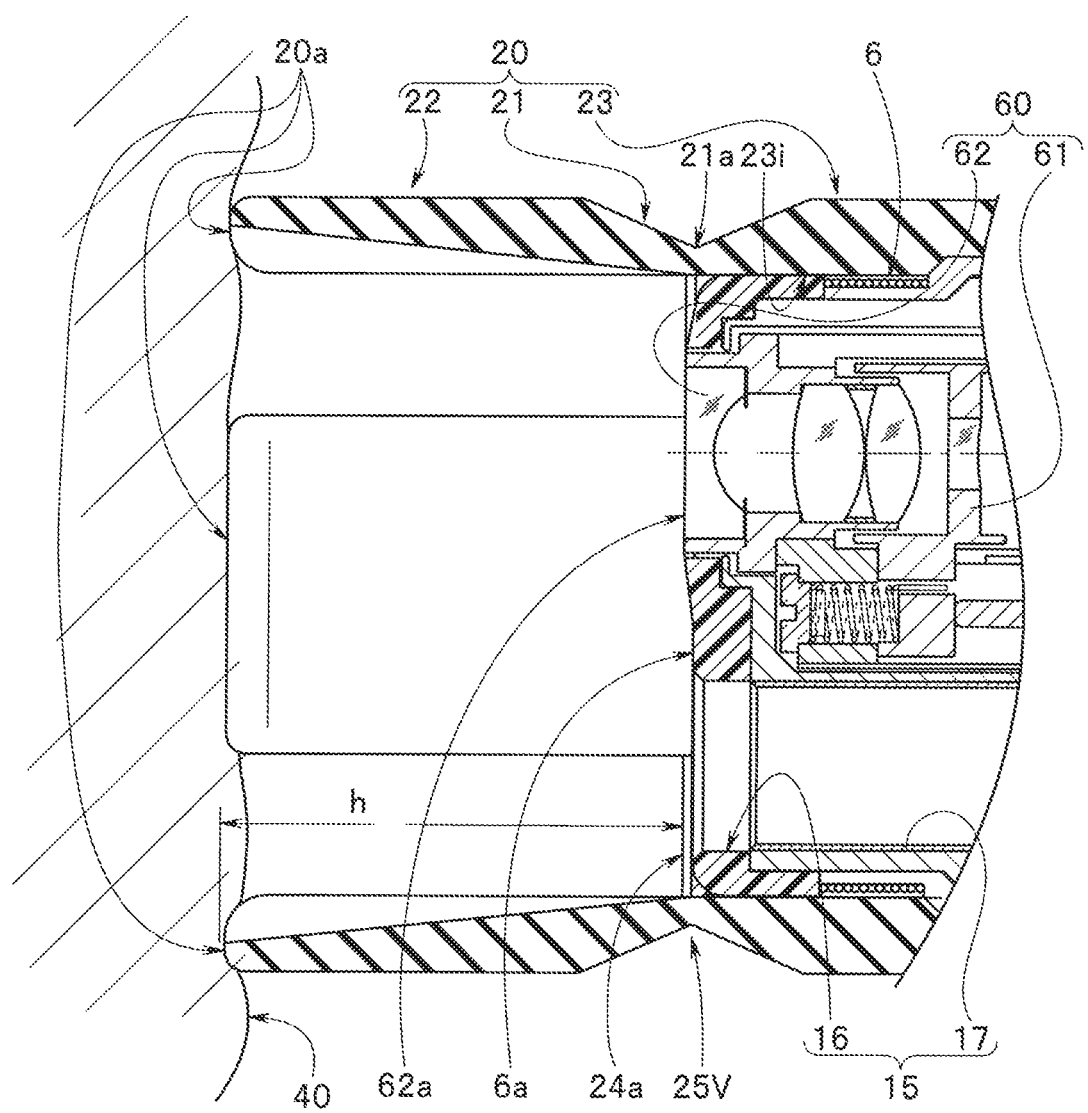
FIG. 3 is a diagram illustrating a magnifying observation state in which the distal end hood is mounted on a distal end portion of the endoscope.

When performing the magnifying observation, as illustrated in FIG. 3, the operator brings the hood distal end surface 20a of the distal end hood 20 mounted on the distal end portion 6 of the endoscope 2 into contact with a subject 40 without elastically deforming the valley fold portion 25V.

Thereby, the lens surface 62a of the distal end lens 62 of the observation optical system 60 is disposed so as to be separated from the subject 40. In the present embodiment, the depth h from the hood distal end surface 20a to the cutout bottom portion 24a of the cutout 24 is set to the observation depth at the time of the magnifying observation of the observation optical system 60.

Then, the separation distance between the lens distal end surface 62a of the distal end lens 62 and the surface of the subject 40 can be maintained at the observation depth, and the magnifying observation can be performed in a stable state.

Figure 4A:
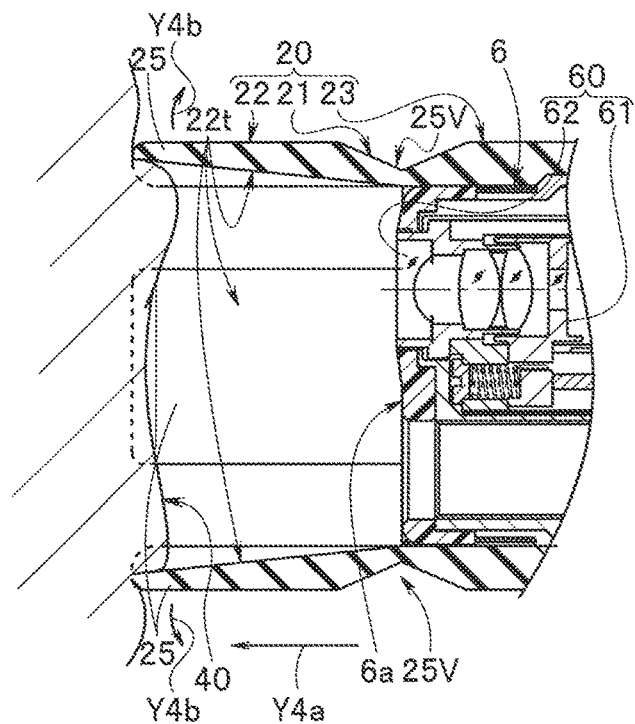
FIG. 4A is a diagram illustrating a shift from the magnifying observation state to a super-magnifying observation state.

On the other hand, when performing the super-magnifying observation, the operator pushes the distal end portion 6 on which the distal end hood 20 is mounted in the direction of arrow Y4a in FIG. 4A with the hood distal end surface 20a of the distal end hood 20 in contact with the subject 40 as illustrated in FIG. 3.

Then, in addition to the hood distal end surface 20a, the tapered surface 22t comes into contact with the subject 40. In this contact state, by further continuing the pushing operation in the direction of arrow Y4A, an external force acts on the tapered surface 22t from the subject 40, and the projection portion 25 is deformed in the direction indicated by arrow Y4b.

Figure 4B:
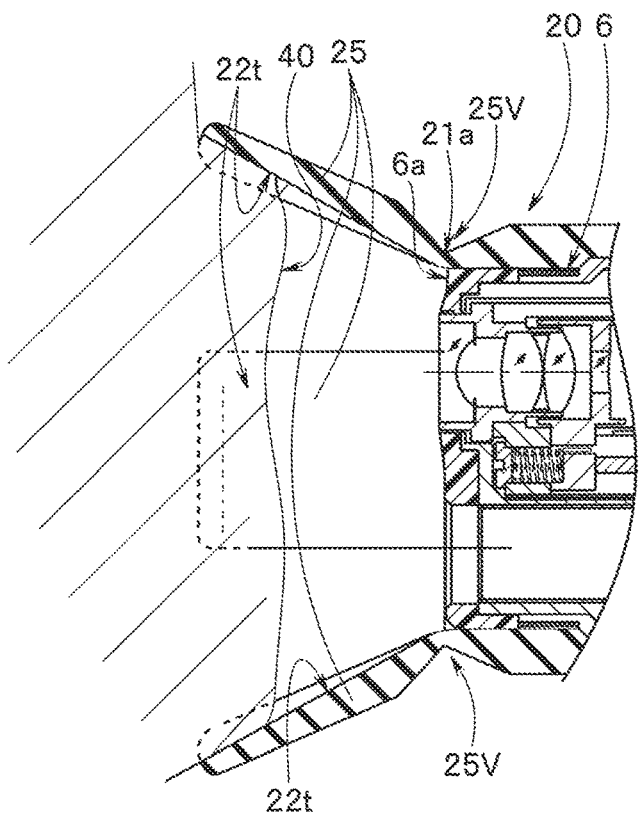
FIG. 4B is a diagram illustrating deformation of a projection portion during the shift.

Then, by continuing the further pushing operation, as illustrated in FIG. 4B, each of the four projection portions 25 is elastically deformed outward with the valley fold portion 25V as the hinge.

Here, the groove bottom portion 21a is located on the front side of the distal end surface 6a, so that the tapered surface 22t is pressed against the subject 40 up to the vicinity of the cutout bottom portion 24a.

Figure 4C:
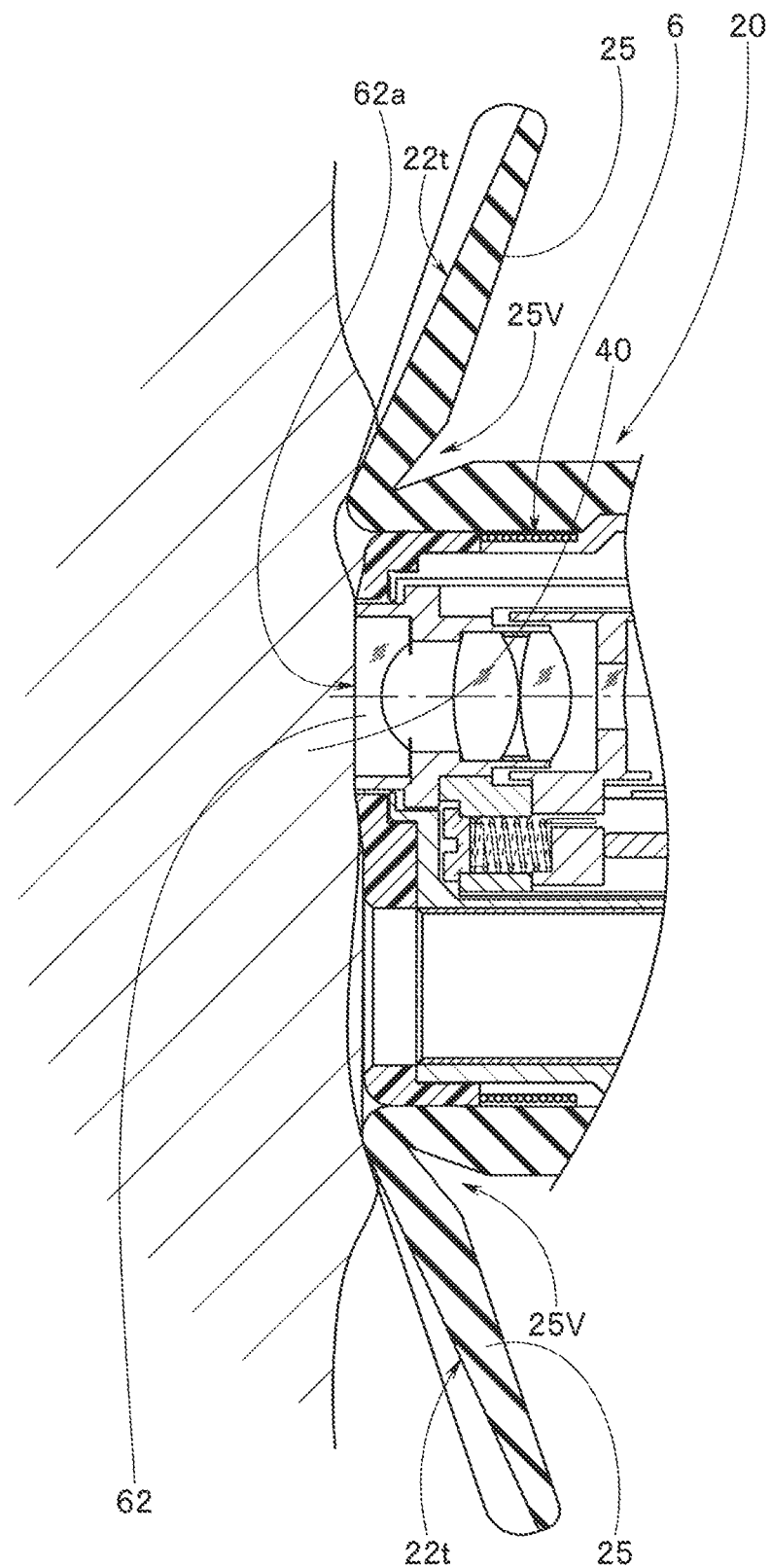
FIG. 4C is a diagram illustrating the super-magnifying observation state.

As a result, as illustrated in FIG. 4C, each projection portion 25 of the distal end hood 20 is deformed into a predetermined bending state with the valley fold portion 25V as the hinge, and the lens distal end surface 62a of the distal end lens 62 is brought into close contact with the subject 40 as the observation target portion. This allows the super-magnifying observation.

As described above, in the distal end hood 20 of the present embodiment, the protruding portion 22 located on the front side of the peripheral groove 21 has the tapered surface 22t. In addition, the protruding portion 22 disposes the plurality of projection portions 25 that are elastically deformable outward by the plurality of cutouts 24 that reach the locking portion 23 with the peripheral groove 21 as the hinge.

According to the configuration, the distal end hood 20 can be formed of one material having a predetermined hardness without being formed of a relatively hard resin material and a resin material softer than the hard resin material.

Then, in the mounted state in which the locking portion 23 of the distal end hood 20 is locked to the distal end portion 6 of the endoscope 2, the hood distal end surface 20a of the distal end hood 20 is held by abutting on the subject 40, so that the distance between the distal end lens 62 and the subject 40 can be stably secured for the magnifying observation.

On the other hand, by bending the projection portion 25 with the valley fold portion 25V as the hinge, the lens distal end surface 62a of the distal end lens 62 is brought into close contact with the subject 40, thus enabling to perform the super-magnifying observation.

Note that, in the embodiment described above, the angle of the V-groove is set so that the projection portion 25 is elastically deformed with the valley fold portion 25V as the hinge, and the lens distal end surface 62a is brought into close contact with the subject 40 without fail. Further, the elastic force around the valley fold portion 25V of the projection portion 25 is set so as to obtain a good magnifying observation state and a good super-magnifying observation state by appropriately setting the shape of the projection portion 25, the groove width and the groove depth of the peripheral groove 21, in addition to the rubber hardness of the distal end hood 20.

Furthermore, by changing the design of the observation optical system of the endoscope 2, it is possible to observe in a state between the magnifying observation state (see FIG. 3) and the super-magnifying observation state (see FIG. 4C), for example, in the intermediate state illustrated in FIG. 4B (the state is referred to as intermediate magnifying observation). When the distal end hood is used for an endoscope capable of performing such intermediate magnifying observation, for example, another peripheral groove that is deeper than the peripheral groove 21 and is easily valley-folded may be provided in front of the peripheral groove 21. In other words, only the added peripheral groove is configured to be valley-folded during the intermediate magnifying observation, so that it is possible to cope with three observation states of the magnifying observation state, the intermediate magnifying observation state, and the super-magnifying observation state.

In the above-described embodiment, in order to ensure the groove bottom portion 21a of the peripheral groove 21 is disposed on the front side of the distal end surface 6a of the distal end portion 6 in the hood-mounted state, the depth h and the distance L are set to be the same, and the cutout bottom portion 24a is disposed on the front side of the distal end surface 6a of the distal end portion 6. However, as illustrated in FIG. 5, a positioning recessed portion 23b for positioning and disposing the distal end portion 6 may be provided on the inner surface of a locking portion 23A of a distal end hood 20A.

As illustrated in FIG. 5, the locking portion 23A of the distal end hood 20A has the positioning recessed portion 23b on an inner peripheral surface 23i. The positioning recessed portion 23b is set so that a recessed portion bottom surface 23c is located on the rear side by a predetermined distance d from the groove bottom portion 21a.

The distance d is identical with the difference in level between the distal end surface 6a and the lens distal end surface 62a.

According to the configuration, when the distal end hood 20A is mounted on the distal end portion 6, the distal end surface 6a of the distal end portion 6 is brought into contact with the recessed portion bottom surface 23c of the positioning recessed portion 23b provided in the distal end hood 20A. Thereby, the locking portion 23A of the distal end hood 20A is locked to the outer peripheral surface 6o of the distal end portion 6, so that the groove bottom portion 21a can be disposed on the front side of the distal end surface 6a without fail.

Further, in the arrangement state, the distance from the hood distal end surface 20a to the lens distal end surface 62a is the observation depth during the magnifying observation. The lens distal end surface 62a protrudes from the distal end surface 6a of the distal end portion 6, which is disposed in contact with the recessed portion bottom surface 23c.

The distal end hoods 20 and 20A described above are provided with the plurality of projection portions 25 on the front side of the locking portions 23 and 23A that are locked to the distal end portion 6 of the endoscope 2. Another configuration example of the distal end hood and the operation thereof will be described with reference to FIGS. 6A to 6D.

Figure 6A:
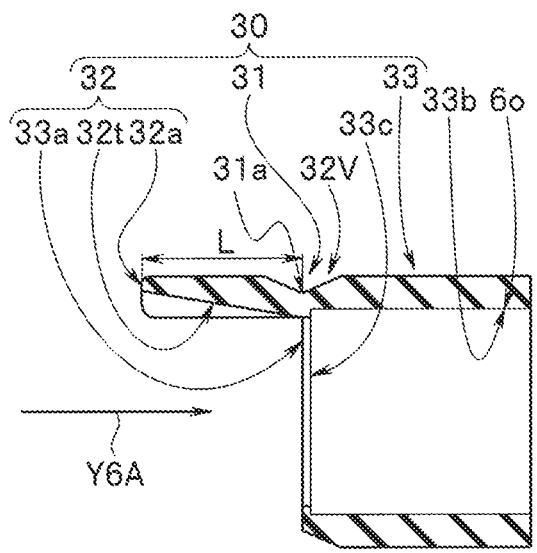
FIG. 6A is a diagram illustrating another configuration example of the distal end hood.

The rubber hardness of a distal end hood 30 illustrated in FIG. 6A is set to be harder than the rubber hardness of the distal end hood 20 in advance.

The distal end hood 30 is provided with one protruding portion 32 having a front outer peripheral surface and a tubular locking portion 33 having a rear outer peripheral surface with a V-groove 31 having a V-shaped cross-section interposed therebetween.

In the present embodiment, the locking portion 33 is provided with a positioning recessed portion 33b that is similar to the positioning recessed portion 23b. The inner peripheral surface of the positioning recessed portion 33b is locked to the outer peripheral surface 6o of the distal end portion 6 of the insertion portion 3. A recessed portion bottom surface denoted by the reference numeral 33c is similar to the recessed portion bottom surface 23c.

Figure 6B:
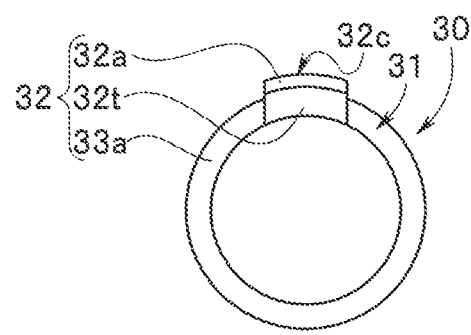
FIG. 6B is a front view of the distal end hood of FIG. 6A viewed from the direction of arrow Y6B.

As illustrated in FIGS. 6A and 6B, the protruding portion 32 has a rectangular shape, and protrudes forward from a locking portion distal end surface 33a, which is one end surface of a predetermined portion of the locking portion 33. In the protruding portion 32, an arc portion 32c is set to have a predetermined length. Note that the protruding portion 32 may have a mountain shape.

An inner surface of the protruding portion 32 is an inclined surface 32t. The wall thickness of the protruding portion 32 having the inclined surface 32t is thinner on the protruding portion front surface 32a side than on the locking portion distal end surface 33a side. In other words, the wall thickness of the protruding portion 32 becomes thinner toward the front, similar to the above-described protruding portion 22.

A groove bottom portion 31a of the V-groove 31 for dividing the outer peripheral surface of the distal end hood 30 is provided along the locking portion distal end surface 33a. The groove bottom portion 31a of the V-groove 31 is provided at a position separated from the protruding portion distal end surface 32a by the distance L.

The V-groove 31 formed on the front outer peripheral surface of the protruding portion 32 functions as a valley fold portion 32V that is a hinge when the protruding portion 32 is bent outward with respect to the locking portion 33. The function of the valley fold portion 32V is the same as the function of the valley fold portion 25V.

Also in the present embodiment, in the hood-mounted state in which the locking portion 33 is locked to the distal end portion 6, the groove bottom portion 31a of the V-groove 31 is disposed on the front side of the distal end surface 6a of the distal end portion 6.

Other configurations are the same as those of the above-described embodiment, and the same members are denoted by the same reference numerals, and description thereof will be omitted.

Here, the operation of the distal end hood 30 will be described.

When performing the super-magnifying observation or the magnifying observation, the operator locks the outer peripheral surface 6o of the distal end portion 6 in the positioning recessed portion 33b of the locking portion 33 of the distal end hood 30. Thereby, as described above, the groove bottom portion 31a is disposed on the front side of the distal end surface 6a of the distal end portion 6.

Figure 6C:
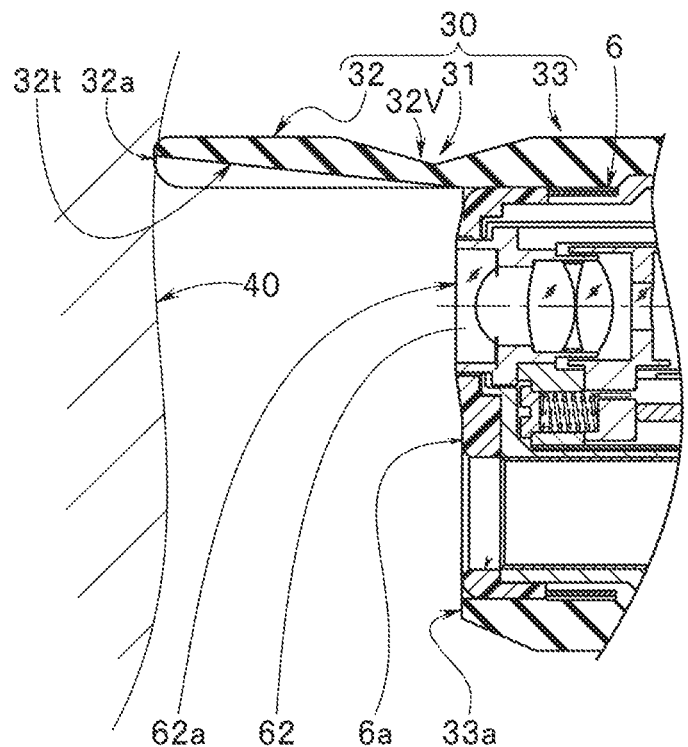
FIG. 6C is a diagram illustrating a magnifying observation state in which the distal end hood illustrated in FIGS. 6A and 6B is mounted on the distal end portion of the endoscope.

When performing the magnifying observation, as illustrated in FIG. 6C, the operator brings the protruding portion front surface 32a of the protruding portion 32 of the distal end hood 30 mounted on the distal end portion 6 of the endoscope 2 into contact with the subject 40.

Thereby, the lens surface 62a of the distal end lens 62 is disposed so as to be separated from the subject 40. In the present embodiment, the distance from the protruding portion front surface 32a to the lens distal end surface 62a is an observation depth during magnifying observation. The lens distal end surface 62a protrudes from the distal end surface 6a of the distal end portion 6, which is disposed in contact with the recessed portion bottom surface 33c.

In the present embodiment, as described above, the rubber hardness of the distal end hood 30 is set to be harder than the rubber hardness of the distal end hood 20. Therefore, in a state in which the protruding portion front surface 32a of the protruding portion 32 of the distal end hood 30 abuts on the subject 40, the distance from the lens distal end surface 62a of the distal end lens 62 to the surface of the subject 40 is stably maintained at the observation depth, and the magnifying observation can be performed without fail.

On the other hand, when performing the super-magnifying observation, instead of a pushing operation for pushing the distal end portion 6 into the subject 40 from the state illustrated in FIG. 6C in which the protruding portion front surface 32a of the distal end hood 30 is in contact with the subject 40, the operator performs a bending operation in which the bending portion 7 is slightly bent in the direction opposite to the direction in which the protruding portion 32 is provided.

Then, by bending the bending portion 7, the protruding portion front surface 32a side is deformed outward with the valley fold portion 32V of the protruding portion 32 as the hinge. Thereafter, the operator performs the pushing operation of pushing the distal end portion 6 toward the subject 40.

As a result, in the same manner as the above-described embodiment, the groove bottom portion 31a is located on the front side of the distal end surface 6a, so that the inclined surface 32*t* is pressed against the subject 40 up to the vicinity of the locking portion distal end surface 33*a*.

Figure 6D:
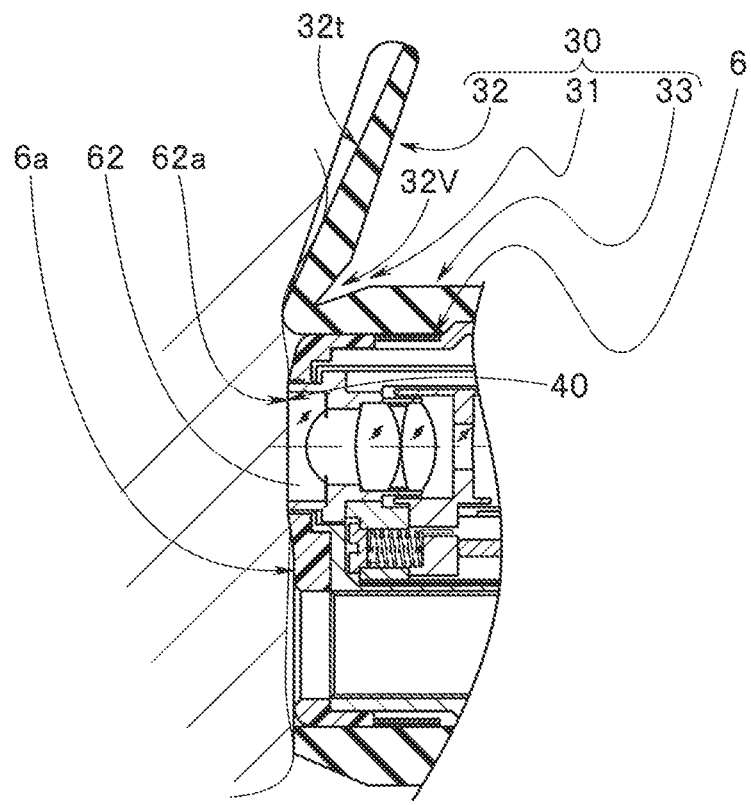
FIG. 6D is a diagram illustrating a super-magnifying observation state in which the distal end hood illustrated in FIGS. 6A and 6B is mounted on the distal end portion of the endoscope.

Then, as illustrated in FIG. 6D, the protruding portion 32 of the distal end hood 30 is deformed into a predetermined bending state with the valley fold portion 32V as the hinge, and the lens distal end surface 62*a* of the distal end lens 62 is brought into close contact with the subject 40 as the observation target portion for the super-magnifying observation.

As described above, the rubber hardness of the distal end hood 30 including the one protruding portion 32 and the locking portion 33 is set to be harder. Thereby, by bringing the protruding portion front surface 32*a* of the protruding portion 32 of the distal end hood 30 into contact with the subject 40, the distance between the distal end lens 62 and the subject can be stably secured for the magnifying observation.

Further, with the protruding portion front surface 32*a* in contact with the subject 40, the bending operation is performed in which the bending portion 7 is slightly bent before the pushing operation is performed. Thereby, after the protruding portion 32 of the distal end hood 30 is bent at the valley fold portion 32V, the pushing operation is performed to bring the lens distal end surface 62*a* of the distal end lens 62 into close contact with the subject 40 for the super-magnifying observation.

Note that the present invention is not limited to the embodiments described above, but various modifications can be made without departing from the spirit and scope of the present invention.

What is claimed is:

1. A distal end hood comprising:
  a hood body comprising:
    a groove having a groove bottom portion formed in a ring shape over an entire circumference at a predetermined position on an outer peripheral surface of the hood body;
    a locking tube configured to be detachably mounted on a distal end portion of an endoscope, the locking tube extending proximally from the groove, and
    a plurality of projections, extending distally from the groove, each of the plurality of projections having an inclined surface on an inner peripheral surface such that a wall thickness of each of the plurality of projections decreases in a distal direction, the inclined surface extending distally relative to the groove;
  wherein each of the plurality of projections are configured to rotate radially outward about the groove bottom portion relative to a longitudinal axis of the hood body; and
  the groove bottom portion is a radially facing surface relative to the longitudinal axis of the hood body.

2. The distal end hood according to claim 1, wherein the locking tube having an inner surface having a step, the step locating a distal end face of the distal end portion of the endoscope at a longitudinal position offset proximally from the groove.

3. An endoscope comprising:
  an insertion section having the distal end portion; and
  the distal end hood according to claim 1 mounted on the distal end portion of the insertion section.

4. The endoscope according to claim 3, wherein
  the distal end portion having a distal lens with a distal lens face; and
  the bottom of the groove is located at a same longitudinal position as the distal lens face.

5. The endoscope according to claim 3, wherein the plurality of projections are configured to rotate such that an end of each of the plurality of projections is proximal to the bottom of the groove in a longitudinal direction of the hood body.

6. The endoscope according to claim 3, wherein
  the insertion section having an observation optical system having an observation depth in a magnifying observation mode;
  the hood body including a cutout provided between adjacent projections of the plurality of projections, and
  a length from a distal end surface of the hood body to a bottom of the cutouts is equal to the observation depth.

7. The distal end hood according to claim 1, wherein the plurality of projections face each other across the longitudinal axis of the hood body when the plurality of projections extend in a longitudinal axis direction.

8. A distal end hood comprising:
  a hood body comprising:
    one or more projections arranged on a distal end of the hood body;
    a groove having a groove bottom portion formed on an outer peripheral surface of the body, the groove being provided proximally to the one or more projections and on at least a circumferential surface of the hood body corresponding to the projection; and
    a locking tube configured to be detachably mounted on a distal end portion of an endoscope, the locking tube extending proximally from the groove,
  wherein each of the one or more projections are configured to rotate radially outward about the groove bottom portion relative to a longitudinal axis of the hood body; and
  each of the one or more projections having an inclined surface on an inner peripheral surface such that a wall thickness of each of the one or more projections decreases in a distal direction, the inclined surface extending distally relative to the groove.

9. The distal end hood of claim 8, wherein the one or more projections comprising a single projection.

10. The distal end hood of claim 8, wherein the one or more projections comprising a plurality of projections.

11. The distal end hood of claim 10, wherein the plurality of projections are equally spaced in a circumferential direction.

12. The distal end hood of claim 10, wherein the plurality of projections face each other across the longitudinal axis of the hood body when the plurality of projections extend in a longitudinal axis direction.

13. The distal end hood of claim 8, wherein the locking tube having an inner surface having a step for locating a distal end face of the distal end portion of the endoscope.

14. The distal end hood of claim 13, wherein the step is positioned to be offset proximally from the groove in a longitudinal axis direction of the hood body.

15. An endoscope comprising:
  an insertion section having the distal end portion; and
  the distal end hood according to claim 8 mounted on the distal end portion of the insertion section.

16. The endoscope of claim 15, wherein
  the distal end portion having a distal lens with a distal lens face; and
  the bottom of the groove is located at a same longitudinal position as the distal lens face.

17. The endoscope of claim 15, wherein the one or more projections are configured to rotate such that an end of each of the one or more projections is proximal to the bottom of the groove in a longitudinal direction of the hood body.

18. The endoscope according to claim 15, wherein the insertion section having an observation optical system having an observation depth in a magnifying observation mode;

the hood body including a cutout provided on each side of the one or more projections, and a length from a distal end surface of the hood body to a bottom of the cutout is equal to the observation depth.

19. A distal end hood comprising:

a hood body comprising:

a groove having a groove bottom portion formed in a ring shape over an entire circumference at a predetermined position on an outer peripheral surface of the hood body;

a locking tube configured to be detachably mounted on a distal end portion of an endoscope, the locking tube extending proximally from the groove, and a plurality of projections, extending distally from the groove, each of the plurality of projections having an inclined surface on an inner peripheral surface such that a wall thickness of each of the plurality of projections decreases in a distal direction, the inclined surface extending distally relative to the groove;

wherein each of the plurality of projections are configured to rotate radially outward about the groove bottom portion relative to a longitudinal axis of the hood body; and wherein the locking tube and the plurality of projections are integrally formed with the groove such that the hood body is a single unitary piece.

20. The distal end hood according to claim 19, wherein the groove bottom portion is a radially facing surface relative to the longitudinal axis of the hood body.

* * * * *